(12) United States Patent
Williams et al.

(10) Patent No.: US 7,220,276 B1
(45) Date of Patent: May 22, 2007

(54) ENDOVASCULAR GRAFT COATINGS

(75) Inventors: Stuart K. Williams, Tucson, AZ (US); David L. Clapper, Shorewood, MN (US)

(73) Assignee: SurModics, Inc., Eden Prairie, MN (US)

( * ) Notice: Subject to any disclaimer, the term of this patent is extended or adjusted under 35 U.S.C. 154(b) by 0 days.

(21) Appl. No.: 09/519,246

(22) Filed: Mar. 6, 2000

(51) Int. Cl.
*A61F 2/06* (2006.01)
(52) U.S. Cl. .................... 623/1.47; 623/1.46; 623/1.48
(58) Field of Classification Search .............. 623/1.13, 623/1.46
See application file for complete search history.

(56) References Cited

U.S. PATENT DOCUMENTS

| | | | |
|---|---|---|---|
| 4,326,532 A | 4/1982 | Hammar | 128/349 |
| 4,722,906 A | 2/1988 | Guire | 436/501 |
| 4,822,361 A | 4/1989 | Okita et al. | 623/12 |
| 4,979,959 A * | 12/1990 | Guire | 435/176 |
| 5,217,492 A | 6/1993 | Guire et al. | 623/11 |
| 5,443,477 A * | 8/1995 | Marin et al. | 606/198 |
| 5,512,329 A | 4/1996 | Guire et al. | 427/508 |
| 5,563,056 A | 10/1996 | Swan et al. | 435/180 |
| 5,575,818 A | 11/1996 | Pinchuk | 623/1 |
| 5,637,460 A | 6/1997 | Swan et al. | 435/6 |
| 5,693,085 A | 12/1997 | Buirge et al. | 623/1 |
| 5,693,088 A | 12/1997 | Lazarus | 623/1 |
| 5,714,360 A | 2/1998 | Swan et al. | 435/174 |
| 5,744,515 A * | 4/1998 | Clapper | 523/113 |
| 5,769,882 A | 6/1998 | Fogarty et al. | 623/1 |
| 5,800,541 A | 9/1998 | Rhee et al. | 623/11 |
| 5,843,158 A | 12/1998 | Lenker et al. | 623/1 |
| 5,874,165 A * | 2/1999 | Drumheller | 428/308.4 |
| 6,280,467 B1 | 8/2001 | Leonhardt | 623/1.16 |
| 6,296,603 B1 * | 10/2001 | Turnlund et al. | 600/3 |
| 6,312,457 B1 | 11/2001 | DiMatteo et al. | 623/1.13 |

FOREIGN PATENT DOCUMENTS

| | | |
|---|---|---|
| EP | 0 608 095 | 7/1994 |
| EP | 1140243 | 12/1999 |
| WO | WO/95/13033 | 5/1995 |
| WO | WO 95/26695 | 10/1995 |
| WO | WO 95/29647 | 11/1995 |
| WO | WO 99/29260 | 6/1999 |
| WO | WO 00/40278 | 7/2000 |

OTHER PUBLICATIONS

Parsons et al, "Diminshed platelet adherence to type V collagen", Arteriosclerosis Nov.-Dec. 1983; 3(6):abstract.*
Kondo, et al., "Endovascular Graft Treatment of Aortic Aneurysms: Future Perspectives", Nippon Geka Gakkai Zasshi 100(8):506-12, (1999) (abstract).
Wain et al., "Endoleaks after Endovascular Graft Treatment of Aortic Aneurysms: Classification, Risk Factors, and Outcome", J Vasc. Surg. 27(1):69-78 (1998) (abstract).
Jacobowitz et al., "The Significance and Management of the Leaking Endograft", Semin. Vasc. Surg. 12(3):199-206 (1999) (abstract).
Colman, R.W., "Mechanisms of Thrombus Formation and Dissolution", Cardiovascular Pathol. 2:23S-31S (1993).
Guidoin, et al., "Collagen Coated Polyester Arterial Prostheses: An Evaluation", Transplantation/Implantation Today, pp. 21-25, Feb. 1988.
Ozaki, et al., "New Stent Technologies", Prog. Cardiovasc. Dis., 39(2):129-40 (Sep.-Oct. 1996) (abstract).
Marois, et al. "In Vivo Biocompatibility and Degradation Studies of Polyhydroxyoctanoate in the Rat: A New Sealant for the Polyester Arterial Prosthesis", Tissue Eng., 5(4):369-386 (1999) (abstract).
Ben Slimane, et al., "Albumin-coated Polyester Arterial Prostheses: Is Xenograft Albumin Safe?", Biomater. Artif. Cells Artif. Organs. 15(2):453-81 (1987) (abstract).
Lee, et al., "Development and Characterization of an Alginate-Impregnated Polyester Vascular Graft.", J. Biomed. Mater. Res., 36(2):200-8 (Aug. 1997) (abstract).
Chafke, et al., "Albumin as a Sealant for a Polyester Vascular Prosthesis: Its Impact on the Healing Sequence in Humans.", J. Cardiovasc. Surg., (Torino) Oct;37(5):431-40 (1996)(abstract).
Ukpabi, et al. "The Gelweave Polyester Arterial Prosthesis", Can. J. Surg., 38(4):322-3 (Aug. 1995) (abstract).
Henry, et al., "A New Access Site Management Tool: the Angio-Seal Hemostatic Puncture Closure Device.", J. Endovasc. Surg., 2(3):289-96 (Aug. 1995) (abstract).
Shin, et al., "Histology and Electron Microscopy of Explanted Bifurcated Endovascular Aortic Grafts: Evidence of Early Incorporation and Healing.", J. Endovasc. Surg., 6(3):246-50 (Aug. 1999)(abstract).
Gates and Kent, Chapter 27 Alternative Bypass Conduits and Methods for Surgical Coronary Revascularization, pp. 291-315 (1994).

* cited by examiner

*Primary Examiner*—Tom Barrett
(74) *Attorney, Agent, or Firm*—SurModics, Inc.; Steven J. Keough

(57) ABSTRACT

An endovascular graft, having both an expandable stent portion and a stent cover portion positioned, the graft itself and/or a stent cover-portion coated with a bioactive agent adapted to promote initial thrombus formation, preferably followed by long term fibrous tissue ingrowth. The endovascular graft prevents endoleaking by promoting a short term hemostatic effect in the perigraft region. This short term effect can, in turn, be used to promote or permit long term fibrous tissue ingrowth. Particularly where the stent cover portion is prepared from a porous material selected from PET and ePTFE, the bioactive agent can include a thrombogenic agent such as collagen covalently attached in the form of a thin, conformal coating on at least the outer surface of the stent cover. An optimal coating of this type is formed by the activation of photoreactive groups.

32 Claims, No Drawings

ENDOVASCULAR GRAFT COATINGS

BACKGROUND OF THE INVENTION

Technical Field

The present invention relates to endovascular grafts, particularly including endovascular grafts that include both a rigid and expandable stent portion and a stent cove portion. In another aspect, the invention relates to the manufacture and use of such devices.

Endovascular grafts (also known by such terms as endoluminal grafts, endografts, endovascular stent grafts, expandable transluminal grafts, vascular endoprostheses, and intravascular stent grafts) can be broadly defined as vascular grafts that are positioned within existing veins and arteries. As such, they can be contrasted with non-endovascular grafts, more commonly known as vascular grafts, which can be provided in the form of either bypass grafts or interpositional grafts. As compared to endovascular grafts, vascular grafts are instead positioned in a manner that replaces a portion (interpositional), or provides a shunt (bypass) between one or more portions, of veins or arteries, or between an artery and a vein. Endovascular grafts have been gaining increased attention in recent years, particularly for use in treating aneurysms such as aortic aneurysms. An aneurysm is generally defined as a sac formed by the pathologic dilation of an artery or vein beyond its normal physiological diameter.

Abdominal aortic aneurysms (AAA), which are aneurysms of the aorta in the abdominal cavity, are of particular interest, as are thoracic aneurysms. See, for example, "Endovascular Graft Treatment of Aortic Aneurysms: Future Perspectives", Kondo, et al., *Nippon Geka Gakkai Zasshi* 100(8):506-12, (1999) (abstract), which describes the manner in which the use of endovascular grafts to treat aortic aneurysms, first clinically applied by Parodi et al., has gained popularity. Although the use of endovascular grafts were initially limited to high-risk patients, their indications have been gradually expanded.

A typical approach involves the initial placement of an endovascular graft in the aneurysm, in order to exclude the aneurysmal sac while maintaining the arterial blood flow, thus preventing further dilation and possible rupture of the vessel. Over recent years, however, Kondo et al. and others have described various instances in which aneurysms, excluded completely during surgery, can became patent due to "endoleaking", a phenomenon that can occur immediately or even years after the procedure. Considering these and other features, some practitioners hold that endovascular grafting should continue to be limited to high-risk patients. In most cases, however, and particularly with thoracic aortic aneurysms, endovascular treatment is considered a useful alternative for those with localized aneurysms because of the high perioperative morbidity accompanying conventional open repair.

With regard to the continuing concern about endoleaking, however, see also Wain, et al., "Endoleaks after Endovascular Graft Treatment of Aortic Aneurysms: Classification, Risk Factors, and Outcome", *J Vasc. Surg.*: 27(1):69-78 (1998) (abstract), which also describes the manner in which incomplete endovascular graft exclusion of an abdominal aortic aneurysm can result in endoleaking.

Finally, see Jacobowitz et al., "The Significance and Management of the Leaking Endograft", *Semin. Vasc. Surg.* 12(3):199-206 (1999) (abstract), which defines endoleaking as the persistence of blood flow outside the lumen of an endograft, but within an aneurysm sac or adjacent vessel being treated by the graft. Diagnosis may be difficult, and treatment remains somewhat controversial. The article discusses the clinical significance and appropriate management of endoleaks within the context of current understanding of this phenomenon.

On another subject, the literature provides several examples of the use of hemostatic agents in the course of surgery. Generally, "hemostasis" can be defined as the interruption of blood flow to any anatomical area. Hemostasis is typically caused by biological processes (such as clot formation) or surgical procedures (including manual compression). The word "thrombosis", in turn, is generally used to refer to hemostasis produced by clot formation. A variety of commercial hemostatic products exist that promote localized clot formation, and which generally incorporate one or more thrombogenic proteins. Such proteins include thrombin and certain collagens, which are known to activate platelets and/or fibrin formation (Colman, R. W.,"Mechanisms of Thrombus Formation and Dissolution", *Cardiovascular Pathol.* 2:23S-31S (1993). The primary use, currently, for such hemostatic products is to halt diffuse bleeding from wound sites, vascular punctures, or other surgical procedures. Examples of such products include FluoSeal Matrix® (Fusion Medical Technologies, Mountain View, Calif.) and CoStasis® (Cohesion Corporation, Palo Alto, Calif.), each of which is composed of thrombin mixed with bovine collagen. Angio-Seal® (Kensey Nash Corporation, Exton, Pa.) is a three-component preparation, one of which is bovine skin collagen. Each of the above hemostatic products consists of two or more components, which are mixed immediately before use.

There is a dichotomy in the medical device industry with regard to the use of thrombogenic coatings on grafts, depending in large part on the diameter of the graft involved. Small diameter grafts (e.g., less than about 6 mm in diameter) are typically not provided with thrombogenic lumenal surfaces, since to do so would tend to promote the rapid accumulation of thrombin on the surface, and/or to speed the invasion and proliferation of myofibroblasts (leading to intimal hyperplasia), either or both of which processes can tend to occlude the graft itself. Typically, therefore, non-thromogenic coatings and materials are commonly preferred for usein preparing small diameter bypass grafts (e.g., peripheral and coronary artery grafts). See, for instance, Ozaki, et al., "New Stent Technologies", *Prog. Cardiovasc. Dis.,* 39(2):129-40 (Sept-Oct 1996) (abstract).

Large diameter vascular grafts, and particularly those intended for use as aortic vascular grafts, are typically not prone to being occluded in a similar fashion. To the contrary, these grafts have a different inherent problem, namely, the tendency of blood to seep through what are typical porous materials used to form the graft itself. Hence these grafts can be, and often are, coated with a hemostatic agent that acts as a barrier to blood flow by physically occluding the pores. The pores of materials such as polyethylene terephthalate (PET), for instance, can be plugged by a variety of methods, including, 1) by preclotting the graft (e.g., dipping the grafts in the patients own blood, to permit clots to form in the pores), or 2) by filling the pores with materials such as crosslinked gelatins.

Hemostatic barrier agents are therefore occasionally used in connection with conventional large diameter vascular (though non-endovascular) grafts. Guidoin, et al., for instance, evaluated three clinically-used PET grafts (available under the tradenames Gelseal™, Hemashield™, and Tascon™) whose pores were filled with gelatin or collagen ("Collagen Coated Polyester Arterial Prostheses: An Evaluation", *Transplantation/Implantation Today*, pp. 21-25, February 1988). With these grafts, the applied gelatin or collagen was crosslinked with either formaldehyde or glutaraldehyde. When evaluated in vitro, the collagen or gelatin "coatings" decreased water flow through the graft walls by more than 99% , therefore confirming that each provided an immediate physical barrier to blood flow. Additional barrier coatings that are reported to block blood flow through the walls of polyester grafts include albumin and alginate.

Similarly, a variety of other coatings have been described for use on large diameter arterial (though again, typically non-endovascular) grafts. See for instance, Marios, et al. "In Vivo Biocompatibility and Degradation Studies of Polyhydroxyoctanoate in the Rat: A New Sealant for the Polyester Arterial Prosthesis", *Tissue Eng.* 5(4):369-386 (1999) (abstract); Ben Slimane, et al., "Albumin-coated Polyester Arterial Prostheses: Is Xenogenic Albumin Safe?", *Biomater. Artif. Cells Artif. Organs.* 15(2):453-81 (1987) (abstract): Lee, et al., "Development and Characterization of an Alginate-impregnated Polyester Vascular Graft", *J. Biomed. Materi. Res.*, 36(2):200-8 (August 1997 ) (abstract); Chafke, et al., "Albumin as a Sealant for a Polyester Vascular Prosthesis: Its Impact on the Healing Sequence in Humans", *J. Cardiovasc. Surg.*, (Torino) Oct;37(5):431-40 (1996)(abstract); and Ukpabi, et al. (abstract). "The Gelweave Polyester Arterial Prosthesis", *Can. J. Surg.*, 38(4):322-3 (August 1995) (abstract).

For reasons that include those above, therefore, it appears that thrombogenic agents have rarely, if ever, been used in any connection with endovascular grafts, and then typically for reasons quite unrelated to either coating the article itself, or in turn, for preventing endoleaking. See, for instance, Henry, et al., "A New Access Site Management Tool: the Angio-Seal Hemostatic Puncture Closure Device", *J. Endovasc. Surg.*, 2(3):289-96 (August 1995) (abstract) suggests that with the increasing number of percutaneously applied endovascular therapies, the incidence of access-related vascular complication can be expected to rise, particularly in association with those techniques requiring large sheaths or anticoagulation. Recognizing the need for a safe, easy to use, and effective hemostatic technique to replace the labor-intensive method of manual compression, the authors describe a bioabsorbable, sheath-delivered vascular device (Angio-Seal) that deposits a small collagen plug within the arterial wall to mechanically seal the puncture defect.

On a separate subject, long-term responses of the body to various materials, including those used to fabricate endovascular grafts, have been studied as well. See, for instance Shin, et al., "Histology and Electron Microscopy of Explanted Bifurcated Endovascular Aortic Grafts: Evidence of Early Incorporation and Healing", *J. Endovasc. Surg.*, 6(3):246-50 (August 1999)(abstract), which reports an examination of explanted bifurcated endovascular aortic grafts for histologic evidence of early healing and incorporation.

However, there are many references in the art that describe the undesirable role of "intimal hyperplasia" in promoting occlusions. See, for instance, Gates and Kent, 1994 in "Alternative Bypass Conduits and Methods for Surgical Coronary Revascularization". Few references, if any, however, describe this or any other process being of long term fibrous tissue ingrowth as being a positive event to be encouraged with a bypass graft, let alone with an endovascular graft.

Finally, and on yet another subject, the assignee of the present invention has previously described a variety of applications for the use of photochemistry, and in particular, photoreactive groups, e.g., for attaching polymers and other molecules to support surfaces. See, for instance, U.S. Pat. Nos. 4,722,906, 4,979,959, 5,217,492, 5,512,329, 5,563,056, 5,637,460, 5,714,360, and 5,744,515.

In spite of these various advances, however, to date there appears to have been little if any progress made with respect to the solving the problem of endoleaking, per se. This in spite of the fact that the widespread acceptance and true value of endovascular grafts are likely to remain hampered until this problem is resolved.

SUMMARY OF THE INVENTION

The present invention comprises an endovascular graft, e.g., in the form of an expandable stent portion and a stent cover portion positioned either within and/or surrounding the expandable portion, the graft (e.g., stent cover portion) being coated with a bioactive agent adapted to promote initial thrombus formation when the graft is positioned within a blood vessel. Optionally, and preferably, the coated stent and/or cover of the present invention also provides improved fibrous tissue ingrowth over time. The term "fibrous tissue ingrowth", as used herein, refers to the repair process that occurs as a response to injury (in this case, the placement of an endovascular graft), by which the body provides new tissue containing a high density of collagen fibers.

In a preferred embodiment, the stent cover portion is prepared from a porous material selected from PET or expanded polytetrafluoroethylene (ePTFE), and the bioactive agent comprises a thrombogenic agent such as collagen. In one preferred embodiment, for instance, the bioactive agent is covalently attached in the form of a thin (e.g., one to three monolayers), and conformal coating on at least the outer surface of stent cover, most preferably by the activation of photoreactive groups provided by either the cover material itself, by the bioactive agent itself, and/or by a linking agent. In another aspect, the invention relates to a method of preparing an endovascular graft that includes coating the graft with a bioactive agent in the manner described herein, as well as a method of using such an endovascular graft to avoid endoleaking upon placement of the graft in vivo. With the endovascular graft in place, and continuity of the vascular lumen reestablished, the coating is preferably adapted to then permit, if not encourage, long term fibrous ingrowth to occur into the stent and/or stent cover. Hence the invention further provides a graft as described herein, positioned within a vein or artery, and preferably, including new fibrous tissue grown into the pores of the graft.

A "conformal" coating, as used herein, refers to one in which the bioactive agent has been carefully attached (e.g., to the individual fibers making up the material, without plugging the pores therein) in a manner that provides an optimal combination of low bulk and effective thrombogenic effect in vivo. By contrast, non-conformal coatings of bioactive agents on a material may provide a thrombogenic effect, but tend to be too bulky to deliver in the manner required. In turn, a conformal coating that provides an inadequate amount of agent, or that provides the agent in a form not suitably tenacious for its intended use, may permit the graft to be delivered in a minimally invasive fashion, but will not tend to provide bioactivity in the desired region, or in an effective amount and duration. Hence the present invention provides an optimal balance between such parameters as bulk, coating density and tenacity, and ultimately, bioactivity in vivo.

DETAILED DESCRIPTION

The method of the present invention can be used in connection with any suitable endovascular graft. Such grafts are typically inserted into the lumen of a blood vessel to form a barrier between the aneurysm and circulating blood, for instance, to treat abdominal aortic aneurysms. The word "perigraft", as used in this context, will refer to the position situated or occurring around an endovascular graft, such that "endoleaking" (also knows as perigraft leaking), can be defined as blood flowing around the endovascular graft and into the aneurysm itself. Such blood flow, therefore, is generally within the perigraft space between the ablumenal surface of the endovascular graft and the surrounding blood vessel. The method and apparatus of this invention can be used to provide acute perigraft hemostasis, that is, hemostasis in the perigraft space, within on the order of an hour or less, and more preferably within several minutes or less, of endovascular graft placement.

Given the present description, those skilled in the art will be able to identify and incorporate a variety of bioactive agents for use as coatings of the present invention. Preferred bioactive agents, for instance, can be selected from those materials presently used as sealants or hemostatic agents in the course of surgery, and preferably those having thrombogenic qualities. The word "thrombosis", and inflections thereof, will be used herein to refer to hemostasis produced by clot formation, and "thrombogenic agents", for instance, to proteins and other agents (e.g. positively charged agents such as chitosan) that actively promote clot formation.

In a preferred embodiment a "bioactive agent" of the present invention will be thrombogenic under the conditions of use. Those skilled in the art will appreciate the manner in which such agents can be identified, coated and used. Preferably, for instance, both the selection of an appropriate bioactive agent and the effectiveness of a coating of the agent upon a stent cover can be evaluated using a "Test Assay" as described herein.

Bioactive agents suitable for use in the present invention include those having a specific action within the body, as well as those having nonspecific actions. Specific action agents are typically proteinaceous, e.g., including thrombogenic types and/or forms of collagen, thrombin and fibrinogen (each of which tend to provide an optimal combination of activity and cost), as well as elastin and von Willebrand factor (which tend to be less active and/or more expensive agents), and active portions and domains of each of these agents. Thrombogenic proteins typically act by means of a specific interaction with either platelets or enzymes that participate in a cascade of events leading eventually to clot formation.

Agents having a nonspecific thrombogenic action are generally positively charged molecules, e.g., polymeric molecules such as chitosan, polylysine, poly(ethylenimine) or acrylics polymerized from acrylamide or methacrylamide which incorporate positively-charged groups in the form of primary, secondary, or tertiary amines or quaternary salts, or non-polymeric agents such as benzalkonium chloride (alkyldimethylbenzylammonium chloride) and TDMAC (tridodecylmethylammonium chloride). Positively charged hemostatic agents promote clot formation by a non-specific mechanism, which includes the physical adsorption of platelets via ionic interactions between the negative charges on the surfaces of the platelets and the positive charges of the agents themselves.

The word "collagen", as used herein, will refer both to native collagen, in which the molecules substantially retain their native triple helix structure, as well as "gelatin", in which the structure has been denatured, resulting in the partial or complete dissociation of the triple helix strands. Native collagens include one or more members of a class of at least 14 proteins, each of which includes a distinctive triple helix as part of its structure. Type I collagen is the most abundant animal protein, is readily isolated, and has useful physical and biological properties. Bovine tendon and skin are two common sources of this collagen, with nearly pure type I collagen being obtained from tendons and skin yielding a mixture of 5% type III and 95% type I collagen. For the above reasons, type I ($\pm$5% type III) is the collagen most commonly used to formulate medical materials (Pachence, J. M., "Collagen-Based Devices for Soft Tissue Repair", J. Biomed. Mater. Res. 33:35-40, 1996). Type I(native) collagen promotes soft tissue repair when incorporated into several types of wound dressings. Collagen type I is also capable of promoting the attachment of fibroblasts and the production of new collagen by such attached fibroblasts.

Another commonly available hemostatic protein is von Willebrand factor, which is reported to mediate the adhesion of platelets to collagen types I, III and VI (Crus et al., "Interaction of the von Willebrand Factor (vWF) with Collagen. Localization of the Primary Collagen-Binding Site by Analysis of Recombinant vWF A Domain Polypeptides", *J. Biol. Chem.*, 270:10822-10827, 1995).

Elastin and fibrinogen are two additional proteins that are abundant in the body, hemostatic, and able to mediate wound healing. Fibrinogen directly promotes platelet aggregation and its product (fibrin) serves as a scaffold for wound healing (Colman, above). The activities of elastin are indirect and are due to its ability to bind types I and III collagens (Dutoya et al., "Unexpected Original Property of Elastin Derived Proteins: Spontaneous Tight Coupling with Natural and Synthetic Polymers" *Biomaterials* 19,147-155 (1998), which in turn are hemostatic and mediate wound healing.

A hemostatic agent will typically be immobilized in an amount between about 0.01 $\mu$g/cm$^2$ to about 50 $\mu$g/cm$^2$ of graft cover material, preferably between about 0.05 $\mu$g/cm$^2$ to about 10 $\mu$g/cm$^2$, and most preferably between about 0.1 $\mu$g/cm$^2$ to about 5 $\mu$g/cm$^2$. Native thrombogenic proteins will typically be active at about the middle of the preferred range (e.g., between about 1 $\mu$g/cm$^2$ and about 10 $\mu$g/cm$^2$), while active peptide segments are likely to be active at about 10-fold lower concentration. Positively charged reagents may require levels toward the upper ends of these concentration ranges, since they tend to act in a non-specific manner.

The endovascular grafts addressed by the application of this invention will typically include both a stent portion adapted to be delivered in a condensed form, and expanded in situ, as well as a cover portion adapted to substantially prevent the flow of blood from the lumen of the vessel itself through the walls and toward the ablumenal surface of the endovascular graft. The cover, in turn, can be of any suitable style or dimensions, e.g., it can cover the internal and/or external portions or surfaces, of some or substantially the entire length, of the expandable stent portion. Optionally, a reagent of this invention can also be used to coat an expandable metallic or polymeric stent with a thrombogenic layer, i.e., without employing or coating a stent cover.

Several such stents can be deployed, for instance, in an overlapping or superimposed manner, such that they effectively provide a substantially impermeable barrier to the flow of blood components. In such an embodiment, one or all of the overlapping stents can be provided with a thrombogenic surface in the manner described herein.

Endovascular grafts in conventional use today typically include an expandable mesh tube covered with a fabric-like cover. The expandable portions are generally formed of a "shape memory" alloy such as nickel titanium alloys (referred to commonly as "nitinol"). Endovascular grafts formed of such materials (including both the stent and cover portions) can be collapsed to form a small diameter tube (e.g., on the order of two mm or less overall diameter), which can be expanded using force and/or by self-expansion, to form a larger diameter tube in situ (e.g., between about six mm and about thirty mm).

The method of the present invention can be adapted for use with a variety of available endovascular grafts and endovascular graft designs, and in particular with "endovascular grafts" that include an expandable (e.g., self-expanding or pressure-expandable) stent portion which is affixed to or formed within a pliable tubular graft. Because of their radial compressibility/expandability, these grafts are particularly useful in applications wherein it is desired to insert the graft into an anatomical passageway (e.g., blood vessel) while the graft is in a radially compact state, and to subsequently expand and anchor the graft to the surrounding wall of the anatomical passageway.

Typically, the stent portions of such endovascular grafts are provided in the form of metallic mesh tubes, e.g., formed in various styles and patterns of intersecting metallic wires, strands or bars, into a structure that permits the endovascular graft to be collapsed or condensed for purposes of its delivery, and once in place, expanded towards its fullest desired diameter (e.g., using a balloon positioned within the device). Once expanded, the resultant endovascular grafts provide a lumen sufficient to restore function to the vessel, and provide an external (ablumenal) surface that abuts the internal surface of the original vessel itself. Materials commonly used or suggested for use as endovascular graft covers include polytetrafluroethylene, expanded polytetrafluroethylene, polyethylene terephthalate, polycarbonate, polyethylene, polyurethane, as well as biodegradable materials such as elastin, polyglycolic acid, and polylactic acid.

Recent methods have been developed for introducing and implanting tubular prosthetic vascular grafts within the lumen of a blood vessel, by percutaneous or minimal incision means. Such endovascular implantation initially involves translumenal delivery of the graft, in a compacted state, by way of a catheter or other transluminally advancable delivery apparatus. Thereafter, the graft is radially expanded and anchored to the surrounding blood vessel wall, thereby holding the graft at its intended site of implantation within the host blood vessel. An affixation method, such as proximal and distal uncovered stent portions sized to over-expand and push into the native vessel wall, can be used to anchor at least the opposite ends of the generally tubular graft to the surrounding blood vessel wall.

One particular application for endovascular grafts of this type is in the treatment of vascular aneurysms, without the need for open surgical access and resection of the aneurysmic blood vessel. Also, such endovascular grafts can also be used to treat occlusive vascular disease—especially, in cases where the graft is constructed in such a manner that the tubular graft material forms a complete barrier between the endovascular graft and the blood flowing through the blood vessel. In this manner the tubular graft material can serve as a smooth, biologically compatible, inner "covering" for the endovascular graft, thereby serving to: a) prevent turbulent blood-flow as the blood flows over the wire members or other structural material of which the endovascular graft is formed; b) prevent immunologic reaction to the metal or other material of which the endovascular graft is formed; and c) provide a barrier to separate a diseased or damaged segment of blood vessel from the blood-flow passing therethrough. The prevention of turbulent blood-flow and/or immunologic reaction to the endovascular graft material are particularly desirable since both phenomena are thought to be associated with thrombus formation and/or restenosis of the blood vessel.

Coated endovascular grafts of the present invention are particularly useful, for instance, in repair of the aorta, vena cava, femoral artery and vein, iliac artery and vein, subclavian artery and vein, tibial artery, peroneal artery, saphenous vein, pulmonary artery and vein, coronary arteries, carotid artery, jugular vein, radial artery, subclavian artery.

In the method of this invention, a bioactive agent is coated on an endovascular graft cover in order to provide the desired level of thrombogenicity (acute hemostasis) under the conditions of deployment and use in vivo. In a preferred embodiment, the coating provides an optimal combination of such properties as low bulk, coating density, coating tenacity, and bioactivity in vivo. Given these functional requirements, and depending on such variables as the type of endovascular graft cover, the method of endovascular graft deployment, and the bioactivity of the agent itself, those skilled in the art will be able to determine an optimal manner of coating a endovascular graft cover for any particular combination of bioactive agent, endovascular graft cover material, and endovascular graft design.

The coating agent of this invention can be coated on the endovascular graft cover in any suitable manner (e.g., by dipping, spraying or brushing) within the skill of those in the relevant art. In a preferred embodiment, a bioactive agent is first derivatized with photogroups, and then brought into contact (i.e., sufficient proximity to permit binding) with a previously formed graft cover. The photoreactive groups are then energized via an external stimulation (e.g, exposure to a suitable light source) to form via free active specie generation, a covalent bond between the agent and either another reagent molecule, the cover surface, or chemical moieties present in the coating solution itself and/or upon the surface. This coating method can be referred to as a "one step" method, since photoreactive coupling chemistry attaches the bioactive agent to the cover surface, and no subsequent steps (other than perhaps washing steps) are required. The external stimulation that is used is preferably in the form of electromagnetic radiation, and preferably is radiation in the ultraviolet, visible or infrared regions of the electromagnetic spectrum.

The coating can be applied at the time of manufacture of the material itself, in the course of its fabrication into a endovascular graft cover, and/or at the time of use. Suitable non-photoreactive methods for coating such materials (in either a covalent or noncovalent fashion) are described in Hoffman, A. S., "Immobilization of Biomolecules and Cells on and within Polymeric Biomaterials", *Clin. Mat.* 11:61-66 (1992).

Other suitable method for covalent coupling to the surface involves an initial step of adding a reactive group to the surface (e.g., amine, carboxyl, etc.), for instance, by the application of ionizing radiation, plasma gas discharge, chemical derivatization, etc. This can be followed by the use of thermochemical crosslinking reagents to couple the hemostatic agent to the surface bound reactive group. Yet other methods can be used to form films around fibers, for instance, using thermochemical crosslinking reagents to crosslink thin films of the hemostatic agent around individual fibers. Other methods, though generally less preferred, can be used to enhance the adsorption of coating agent to the material, e.g., denucleation in ethanol followed by adsorption from phosphate buffered saline (PBS) (see, e.g., Poole-Warren et. al., *J. Biomed. Mater. Res.*, 30:221-229 (1996) used this method to adsorb fibronectin onto ePTFE). In yet another approach, hydrophobic "anchor" groups are added to the hemostatic agent to increase adsorption to implant device polymers. Haverstick, et. al., *Trans. Soc. Biomat.*, 22:287 (1999) have used this method to immobilize ECM peptides onto hydrophobic substrates.

In one preferred embodiment, for instance, a thin, conformal coating of this invention is provided on the perigraft surface (i.e., the external, vessel-contacting surface of the graft itself) and optionally within the pores of the material itself. The coating agent is preferably not coated on the interior (luminal) surface of the graft, since its presence there is likely to be inconsequential at best, and detrimental at worst. The coating agent can be coated, for instance, as a thin conforming layer on and/or around individual fibers of the graft.

A coating of the present invention will typically not add significantly to the bulk of the graft, or interfere with its delivery via a catheter. Nor, in turn, will it interfere with (and preferably will enhance) long term ingrowth by fibrous tissue. Surprisingly, it has been found that bioactive agents can be coated in a manner that provides suitable physical qualities (e.g., bulk, tenacity), chemical qualities (e.g., biocompatibility), and biological qualities (e.g., hemostatic activity) sufficient to lessen or avoid endoleaking yet permit the graft to be delivered and positioned in a minimally invasive fashion (typically, through a catheter). In a preferred embodiment, an effective coating of this invention adds about 25%, or less, preferably about 10%, or less, and most preferably about 5%, or less, to the original thickness of the material used as the stent cover portion. In this manner the resultant endovascular graft can be packaged and delivered in substantially the manner originally intended by the manufacturer.

Typically, it is not desirable to have the coating fill the pores within the graft. The coating agent can be attached to the surface in any suitable manner, e.g., it can be passively adsorbed, entrapped, or covalently bound to the surface itself, or to a coating that is itself positioned within or upon the surface, so long as the coating is sufficiently tenacious and effective for its intended use (e.g., is not removed by flowing blood or by the abrasion associated with delivery via catheter). As such, the coating can be in any suitable form, e.g., impregnated within the pores of the cover itself, as a discrete layer thereon, or as a coating (e.g., film) around the individual fibers of a fabric.

Preferably, the coating agent is covalently attached by photochemical means, e.g., in the manner described in the approaches described in U.S. Pat. Nos. 4,722,906, 4,979,959, 5,217,492, 5,512,329, 5,563,056, 5,637,460, 5,714,360, and 5,744,515. In a particularly preferred embodiment, for instance, various types of collagen can be photoderivatized (e.g., with BBA—EAC—NOS) and radiolabeled using protocols for derivatizing proteins as described in U.S. Pat. No. 5,744,515; columns 13 and 14 (Method and Implantable Article for Promoting Endothelialization).

A preferred composition of this invention includes one or more pendent latent reactive (preferably photoreactive) groups covalently attached, directly or indirectly, to either the surface of the endovascular graft cover, to the bioactive agent itself, or to a linking moiety for use in attaching an agent to a surface. Photoreactive groups are defined herein, and preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules.

The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet and visible portions of the spectrum are preferred and may be referred to herein occasionally as "photochemical group" or "photogroup".

Photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g, ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g, carbon—hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

The azides constitute a preferred class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH=C=O) such as ketene and diphenylketene.

Upon activation of the photoreactive groups, the reagent molecules are covalently bound to each other and/or to the material surface by covalent bonds through residues of the photoreactive groups. Exemplary photoreactive groups, and their residues upon activation, are shown as follows (where R and R' are independently non-interfering organic radicals):

| Photoreactive | Group | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—$SO_2$—NH—R' |
| phosphoryl azides | phosphoramide | $(RO)_2$PO—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

TEST ASSAY

An assay can be performed in the following manner in order to evaluate the usefulness of a particular bioactive agent and manner of coating. The assay, based on a canine model, is used to evaluate and predict the manner and/or extent to which an endovascular graft (the cover portion of which has been treated with a bioactive agent) can prevent endoleaking when positioned in vivo. The canine model has been extensively used to evaluate the in vivo performance of vascular grafts, and Applicants have determined the manner in which the intercostal arteries in the dog provide a unique ability to evaluate endoleaking.

A standard endovascular graft is provided, e.g., in the form of a hook-less, nitinol spring graft system covered with a polymeric (e.g., PET) material. The device cover is coated with the bioactive agent to be evaluated for use in preventing endoleaking. At the end of the implant phase (12 weeks) the animals are anesthetized and the grafts removed. Upon recovery, the grafts are processed for light microscopy.

The grafts are inserted through the femoral artery and placed in the aorta of a dog, just distal to the renal artery. After insertion, an angiogram (at about 30 minutes) is performed to evaluate perigraft blood flow, which is visualized as blood flowing through adjacent intercostal arteries (and particularly those in the region of the aorta that are covered by the endovascular graft). Grafts with an effective coating will substantially prevent both acute and long-term blood flow through adjacent intercostal arteries. Uncoated grafts (or unsuitably coated grafts), by comparison, will not prevent acute perigraft blood flow; however some such grafts may prevent blood flow at 12 weeks.

In addition, the grafts and adjacent aorta are removed at 12 weeks, fixed and evaluated histologically for tissue ingrowth. Grafts with an effective coating will preferably also have the perigraft region largely filled with stable tissue (smooth muscle cells and/or myofibroblasts). Uncoated grafts may have channels through which blood flows from the lumen of the aorta into the perigraft space and out through the intercostal arteries. If the dog model reproduced results observed in human patients, about 20-25% of the uncoated grafts at 12 weeks would show perigraft blood flow during angiography and corresponding perigraft blood channels upon histological evaluation.

In evaluation and comparing uncoated (or unsuitably) coated grafts with those coated in the manner presently described, it can be seen that detectable endoleaking will occur in substantially none (<5%) of coated grafts when evaluated one-half hour after placement (the initial angiogram). By comparison, substantially all (>95%) of the uncoated (or unsuitably) coated grafts will show detectable endoleaking. At 12 weeks, it can be seen that the coated grafts of this invention will continue to prevent detectable endoleaking in substantially all cases (i.e., detectable endoleaking in less than 5% of the cases), as compared to the uncoated grafts, in which detectable endoleaking is likely to continue in up to 20% of the cases.

PROTOCOL

12 Canine animals are used (conditioned mongrels, approx. 27-45 kg, may include both sexes). A pretrial screen is performed to ensure the good general health status of the animals. On the day of surgery, the animals are premedicated with a mixture of intramuscular ketamine, acepromazine and atropine. General anesthesia is induced using intravenous pentothal and the airway maintained with orotracheal intubation. Anesthesia is maintained with a mixture of inhaled halothane and oxygen. The inner thigh is shaved and prepared with betadine. Intravenous cephalexin 500 mg is given prior to the initial incision.

For deploying the graft the inner thigh is prepared for a cut-down to the femoral artery. Heparin is administered, 3,000 units IV, prior to catheter insertion. The femoral artery is isolated and an arteriotomy performed on the artery. A 7 to 9 FR introducer sheath is inserted in the artery. An angiographic catheter is introduced and an angiogram is performed. All angiographic and fluoroscopic procedures are recorded on VCR. The aortic-iliac vasculature is mapped with the diameter of the aorta measured and location of the renal arteries determined. A guide wire is inserted and the catheter removed. The endovascular graft is then inserted over the guide wire and advanced to the proximal position below the renal arteries. Once the device is in the proper position, the central balloon catheter is withdrawn and inflated along the entire length of the device as per the manufacturer's procedures. The delivery catheter is removed and the sheath and angiographic catheter replaced in the vessel. An angiogram is performed and any abnormalities are observed. If abnormalities are observed, the balloon catheter may be reintroduced to correct the situation. The catheter, guide wire and sheath are removed and the arteriotomy repaired. The incision is closed and the dog recovered.

An additional angiogram is performed 30 minutes after implantation to evaluate perigraft blood flow, as indicated by flow through intercostal arteries in the region of the aorta that is covered by the endovascular graft. At 12 weeks, the dogs are re-anesthetized and another angiogram is performed to evaluate perigraft blood flow. Then the grafts are surgically recovered. The graft is exposed under aseptic sterile conditions through an abdominal midline laparotomy. Heparin is administered IV five minutes prior to clamping of the aorta proximal and distal to the endovascular graft. Photographs are taken of the graft in situ. The graft is excised with at least 2 cm of the aorta at both anastomoses. The excised graft is placed in sterile buffer (Dulbecco's CF PBS; pH 7.4 with 1% bovine serum albumin). Animals are euthanized after graft harvest using intravenous B-euthanasia-D® solution. The graft is cut into sections, placed in labeled containers with Histochoice™ fixative for light microscopy.

Each graft is stained with hematoxylin/eosin (H&E) and Masson trichrome. The samples are also immunostained for von Willebrand factor (vWF), α smooth muscle cell actin (αSMC actin) and proliferating cell nuclear antigen (PCNA). The slides are examined and photomicrographs taken. In addition, the slides are analyzed for neointimal thickness. Cells both within the graft and in the tissue associated with the graft are characterized.

DATA ANALYSIS

Angiographic evaluation of grafts with an effective coating of this invention will show unimpeded blood flow through the lumen of the graft but no blood flow through adjacent intercostal arteries when evaluated at either the initial angiogram after implantation or at 12 weeks. In addition, histological evaluation of such grafts at 12 weeks preferably shows the perigraft space to be filled with a high density of cells that stain positive with αSMS actin (smooth muscle cells and/or myofibroblasts). The perigraft space around such grafts lacks channels that would allow blood to flow from the aorta to the intercostal arteries. The lumen of such grafts does not contain sufficient thrombus or layers of cells to significantly reduce blood flow through the aorta. Uncoated grafts or grafts with unsuitable coatings produce two types of detrimental features, namely either: 1) blood flow from the aorta through channels in the perigraft space and into intercostal arteries, and/or 2) the formation of thrombus or excessive layers of cells on the luminal surface, which significantly decreased blood flow through the aorta.

The invention will be further described with reference to the following non-limiting Example, It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLE

Four dogs were studied in the manner described above, with two dogs receiving uncoated grafts and two receiving grafts coated with collagen.

Bovine skin collagen (Semed S Powder) was purchased form Kensey Nash Corporation (Exton, Pa.). This collagen has the proportions of type I collagen (95%) and type III collagen (5%) that are usual for skin-derived collagens. Such collagen is abbreviated below as Col I-S. Col I-S was photoderivatized by the addition of (benzoylbenzoic acid)—(epsilon aminocaproic acid)—(N-oxysuccinimide)(BBA—EAC—NOS) and radiolabeled using protocols described in U.S. Pat. No. 5,744,515 (columns 13 and 14). Photoderivatized Col I-S is abbreviated below as photo-Col I-S.

The coating procedure consisted of immersing endovascular grafts in a solution of photo-COl I-S, removing the grafts, and illuminating for 2.5 minutes at 320 to 340 nm to activate the BBA moieties and produce covalent coupling. The above coating steps were repeated to generate 2 coats of photo-Col I-S. The coated grafts were then washed in sterile phosphate buffered saline (PBS) to remove loosely adherent photo-Col I-S, sterilized by soaking for 30 minutes in 70% ethanol, and washed in sterile PBS to remove ethanol. Coated grafts were stored prior to implantation at 4° C. in PBS plus antibiotics (10 units penicillin G, 10 μg steptromycin, 0.025 μg amphotericin B per ml).

The amount of immobilized photo-Col I-S was quantitated by applying tritium-labeled photo-Col I-S as described above and measuring retained counts via standard liquid scintillation spectrometry methods. The amount of immobilized photo-Col I-S was found to be 1.8 μg of photo-Col I-S per square cm of endovascular graft material. The coating process can be shown to immobilized photo-Col-I-S in a conformal manner, in that the coating is substantially uniform in coverage, but does not significantly fill the pores between adjacent polymer fibers (less than 10% of the pore volume is filled by the coating material). Coating conformity can be evaluated by staining coated grafts with FITC (fluorescein-5-isothiocyanate) and viewing the stained grafts via fluorescence microscopy. When stained and viewed in this manner the individual polymer fibers of the coated endovascular grafts appear uniformly green in color, with the spaces between such fibers appearing black (i.e., unfilled).

During the implant procedures all device deployed easily. The use of a balloon catheter following initial deployment completed the expansion of the devices. Angiograms performed following device deployment revealed unimpeded flow through the lumen of each of the devices. Endoleaking was not detected in either of the coated grafts, but was detected in both of the uncoated grafts, as evidenced by contrast agent present in branch vessels off the aorta. Comparison of device position, both before and after re-establishment of blood flow, indicated that all devices remained in their initial position with no evidence of device movement within the aorta. At the time of device explanation (12 weeks), a repeat angiogram was performed. Neither coated nor uncoated grafts showed blood flow through intercostal arteries, evidence of gross lumenal thickening, or loss of lumenal patency.

All explant samples were subjected to histologic evaluation which included hematoxylin and eosin (H&E) staining, and immunocytochemical evaluation of von Willebrand factor positive cells (endothelium), alpha smooth muscle cell actin positive cells (smooth muscle/myofibroblasts), and proliferating cell nuclear antigen positive cells (cell proliferation/hyperplasia).

Microscopic evaluation of H&E stained sections revealed no significant difference between coated and uncoated grafts. A cellular lining (defined as a neointima) was evident of all samples; however, the thickness of neointima was not sufficient to significantly decrease the lumenal diameter. No thrombus formation was observed.

Immunocytochemistry confirmed the presence of endothelial cells on the lumenal surface (positive staining with vWF antibodies). The cell layers under the endothelium (in the neointima, within the fibers of the graft, and in the perivascular space) were composed predominantly of cells that stained positive with antibodies to αSMC actin, suggesting the predominance of smooth muscle cells or myofibroblasts.

What is claimed is:

1. An endovascular graft comprising an expandable stent portion and a stent cover portion, wherein the stent cover portion comprises a porous, fibrous material having both an outer perigraft surface and an inner luminal surface, and is coated on at least the outer surface with a hemostatic bioactive agent covalently attached by the activation of photoreactive groups provided by the stent cover portion, by the bioactive agent, and/or by a linking agent in the form of a thin, conformal coating in a manner sufficient to prevent endoleaking, wherein the conformal coating comprises the bioactive agent attached to the fibers of the material without occluding its pores or adding more than 25% to the original thickness of the material used as the stent cover portion.

2. A graft according to claim 1 wherein the stent cover portion is prepared from a porous material selected form PET and ePTFE and the bioactive agent comprises hemostatic collagen.

3. A graft according to claim 1 wherein the agent is selected from the group consisting of proteins having a specific hemostatic effect, and positively charged compounds having a nonspecific hemostatic effect.

4. A graft according to claim 3 wherein the agent comprises a protein or the active portions and domains of a protein selected from the group consisting of collagen, thrombin, fibrinogen, elastin and von Willebrand factor.

5. An endovascular graft comprising an expandable stent portion and a porous stent cover portion selected from PET and ePTFE, the porous stent cover portion being coated with a bioactive agent comprising Type I collagen, wherein the collagen is covalently attached in a thin, conformal coating to the porous stent cover portion in a manner sufficient to prevent endoleaking and promote long term fibrous tissue ingrowth, and wherein the coating is covalently attached by the activation of photoreactive groups provided by the porous stent cover portion, by the bioactive agent, and/or by a linking agent and the coating adds no more than 25% to the original thickness of the material used as the stent cover portion.

6. A method of preparing an endovascular graft comprising an expandable stent portion and a stent cover portion, comprising the step of coating at least the outer surface of the stent cover portion with a hemostatic bioactive agent that is covalently attached by the activation of photoreactive groups provided by the stent cover portion, by the bioactive agent, and/or by a linking agent in the form of a thin, conformal coating in a manner sufficient to prevent endoleaking, wherein the coating adds no more than 25% to the original thickness of the material used as the stent cover portion.

7. A method according to claim 6 wherein the stent cover portion is prepared from a porous material selected form PET and ePTFE and the bioactive agent comprises hemostatic collagen.

8. A method according to claim 6 wherein the agent is selected from the group consisting of proteins having a specific hemostatic effect, and positively charged compounds having a nonspecific hemostatic effect.

9. A method according to claim 8 wherein the agent comprises a protein or the active portions and domains of a protein selected from the group consisting of hemostatic collagen, thrombin, fibrinogen, elastin, and von Willebrand factor.

10. A method of preventing endoleaking in the course of deploying and using an endovascular graft that comprises an expandable stent portion and a stent cover, the method comprising the step of first coating the stent cover by a method that comprises the step of coating at least the outer surface of the stent cover portion with a hemostatic bioactive agent that is covalently attached by the activation of photoreactive groups provided by the stent cover portion, by the bioactive agent, and/or by a linking agent in the form of a thin, conformal coating that adds no more than 25% to the original thickness of the material used as the stent cover portion.

11. A method according to claim 10 wherein the stent cover portion is prepared from a porous material selected from PET and ePTFE and the bioactive agent comprises hemostatic collagen.

12. A method according to claim 10 wherein the agent is selected from the group consisting of proteins having a specific hemostatic effect, and positively charged compounds having a nonspecific hemostatic effect.

13. A method according to claim 12 wherein the agent comprises a protein or the active portions and domains of a protein selected from the group consisting of hemostatic collagen, thrombin, fibrinogen, elastin and von Willebrand factor.

14. A method according to claim 10 wherein the endovascular graft comprises an expandable stent portion and a porous stent cover portion selected form PET and ePTFE, and the bioactive agent comprises a protein or the active portions and domains of a protein selected from the group consisting of hemostatic collagen, thrombin, fibrinogen, elastin and von Willebrand factor.

15. A method according to claim 10 wherein the coating is provided on the perigraft, as opposed to luminal, surface of the stent cover.

16. A method according to claim 10 wherein the coating adds about 5%, or less, to the original thickness of the material used as the stent cover portion.

17. A method according to claim 10 wherein the bioactive agent used to coat the surface is itself photoderivatized.

18. A method according to claim 10 wherein the stent cover portion is prepared from a porous material selected from PET and ePTFE, the agent comprises a protein or the active portions and domains of a protein selected from the group consisting of hemostatic collagen, thrombin, fibrinogen, elastin and von Willebrand factor, the coating is provided on the perigraft, as opposed to luminal, surface of the stent cover and adds about 5% or less, to the original thickness of the material used as the stent cover portion.

19. A method according to claim 18 wherein the bioactive agent used to coat the surface is itself photoderivatized.

20. A method of preventing endoleaking in the course of deploying and using an endovascular graft, the method comprising the steps of:

a) providing an endovascular graft comprising an expandable stent portion and a stent cover portion, wherein the stent cover portion comprises a porous, fibrous material having both an outer perigraft surface and an inner luminal surface, the cover portion having a hemostatic bioactive agent on at least the outer surface in the form of a thin, conformal coating covalently attached to the fibers of the material without occluding its pores, by the activation of photoreactive groups provided by the stent cover portion, by the bioactive agent, and/or by a linking agent, wherein the coating does not add more than 25% to the thickness of the material used as the stent cover portion, and b) implanting the stent in the vessel in a manner that avoids endoleaking.

21. A method according to claim 20 wherein the stent cover portion is prepared from a porous material selected from PET and ePTFE and the bioactive agent comprises hemostatic collagen.

22. A method according to claim 20 wherein the agent is selected from the group consisting of proteins having a specific hemostatic effect, and positively charged compounds having a nonspecific hemostatic effect.

23. A method according to claim 22 wherein the agent comprises a protein or the active portions and domains of a protein selected from the group consisting of hemostatic collagen, thrombin, fibrinogen, elastin and von Willebrand factor.

24. A method according to claim 20 wherein the endovascular graft comprises an expandable stent portion and a porous stent cover portion selected for PET and ePTFE, and the bioactive agent comprises a protein or the active portions and domains of a protein selected from the group consisting of hemostatic collagen, thrombin, fibrinogen, elastin and von Willebrand factor.

25. A method according to claim 20 wherein the coating is provided on the perigraft, as opposed to luminal, surface of the stent cover.

26. A method according to claim 20 wherein the coating adds about 5%, or less, to the original thickness of the material used as the stent cover portion.

27. A method according to claim 20 wherein the bioactive agent used to coat the surface is itself photoderivatized.

28. A method according to claim 20 wherein the stent cover portion is prepared from a porous material selected from PET and ePTFE, the agent comprises a protein or the active portions and domains of a protein selected from the group consisting of hemostatic collagen, thrombin, fibrinogen, elastin and von Willebrand factor, the coating is provided on the perigraft, as opposed to luminal, surface of the stent cover and adds about 5%, or less, to the original thickness of the material used as the stent cover portion.

29. A method according to claim 28 wherein the bioactive agent used to coat the surface is itself photoderivatized.

30. A method according to claim 20 wherein the agent is immobilized in an amount between about 0.05 µg/cm$^2$ to about 10 µg/cm$^2$.

31. A method according to claim 20 wherein the endovascular graft is provided in the form of a collapsed small diameter tube of on the order of two mm or less overall diameter, and can be expanded to form a larger diameter tube in situ of between about six mm and about thirty mm.

32. A method according to claim 28 wherein the bioactive agent used to coat the surface is itself photoderivatized, and is immobilized in an amount between about 0.05 µg/cm$^2$ to about 10 µg/cm$^2$, and wherein the endovascular graft is provided in the form of a collapsed small diameter tube of on the order of two mm or less overall diameter, and can be expanded to form a larger diameter tube in situ of between about six mm and about thirty mm.

* * * * *